US009946339B2

(12) United States Patent
Guo et al.

(10) Patent No.: US 9,946,339 B2
(45) Date of Patent: Apr. 17, 2018

(54) GAZE TRACKING THROUGH EYEWEAR

(71) Applicant: Microsoft Technology Licensing, LLC, Redmond, WA (US)

(72) Inventors: Huimin Guo, Bellevue, WA (US); Ibrahim Eden, Redmond, WA (US); Vaibhav Thukral, Kirkland, WA (US); David Zachris Nister, Bellevue, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 266 days.

(21) Appl. No.: 14/509,976

(22) Filed: Oct. 8, 2014

(65) Prior Publication Data
US 2016/0103484 A1   Apr. 14, 2016

(51) Int. Cl.
*G06F 3/01* (2006.01)
*G06K 9/20* (2006.01)
*G06K 9/00* (2006.01)
*G06F 3/00* (2006.01)

(52) U.S. Cl.
CPC .............. *G06F 3/013* (2013.01); *G06F 3/005* (2013.01); *G06K 9/0061* (2013.01); *G06K 9/00604* (2013.01); *G06K 9/2027* (2013.01)

(58) Field of Classification Search
CPC ....... G06F 3/013; G06F 3/005; G06K 9/2027; G06K 9/0061; G06K 9/00604
See application file for complete search history.

(56) References Cited

U.S. PATENT DOCUMENTS 5,471,542 A * 11/1995 Ragland ................. A61B 3/113
                                                        351/208
6,134,339 A * 10/2000 Luo ..................... G06K 9/00604
                                                        382/115
(Continued)

FOREIGN PATENT DOCUMENTS

WO          0249506 A1       6/2002
WO      WO2014181775        * 11/2014  ............... A61B 3/11

OTHER PUBLICATIONS

Y. Ebisawa, Improved Video-Based Eye-Gaze Detection Method, May 10-12, Intrumentation and Measurement Technology conference proceedding, 10th Anniversary. Advanced Technologies in I &M,. 1994 IEEE, pp. 963-966.*

(Continued)

*Primary Examiner* — Mihir K Rayan
(74) *Attorney, Agent, or Firm* — Alleman Hall Creasman & Tuttle LLP

(57) ABSTRACT

A method to furnish input representing gaze direction in a computer system operatively coupled to a vision system. In this method, a first image of an eye at a first level of illumination is acquired by a camera of the vision system. The first image is obtained from the camera, and a second image of the eye corresponding to a second, different level of illumination is also obtained. Brightness of corresponding pixels of the first and second images is compared in order to distinguish a reflection of the illumination by the eye from a reflection of the illumination by eyewear. The input is then furnished based on the reflection of the illumination by the eye.

19 Claims, 7 Drawing Sheets

(56) References Cited

U.S. PATENT DOCUMENTS

| | | | | |
|---|---|---|---|---|
| 6,152,563 | A * | 11/2000 | Hutchinson | A61B 3/113 351/209 |
| 8,457,352 | B2 | 6/2013 | Hennessey et al. | |
| 8,971,570 | B1 * | 3/2015 | Raffle | G06K 9/00604 382/103 |
| 2002/0075384 | A1 | 6/2002 | Harman | |
| 2005/0175218 | A1 | 8/2005 | Vertegaal et al. | |
| 2007/0040908 | A1 | 2/2007 | Cleveland et al. | |
| 2011/0019874 | A1 * | 1/2011 | Jarvenpaa | G06F 3/013 382/103 |
| 2012/0147328 | A1 * | 6/2012 | Yahav | A61B 3/113 351/210 |
| 2012/0154536 | A1 | 6/2012 | Stoker et al. | |
| 2013/0178287 | A1 * | 7/2013 | Yahav | G02B 27/01 463/32 |
| 2015/0085250 | A1 * | 3/2015 | Larsen | G06K 9/00604 351/206 |
| 2015/0145777 | A1 * | 5/2015 | He | G06K 9/0061 345/158 |
| 2015/0199006 | A1 * | 7/2015 | He | G06F 3/013 345/158 |
| 2015/0310253 | A1 * | 10/2015 | Agrawal | G06K 9/0061 382/103 |
| 2016/0125241 | A1 * | 5/2016 | Ebisawa | G06K 9/00604 348/78 |

OTHER PUBLICATIONS

Ebisawa, Y., "Improved Video-Based Eye-Gaze Detection Method", In Proceedings of IEEE Transactions on Instrumentation and Measurement, vol. 47, No. 4, Aug. 1998, 8 pages.

Park, K., "Vision-Based Facial and Eye Gaze Tracking System", In Proceedings of 27th Annual German Conference on AI, KI 2004: Advances in Artificial Intelligence, Sep. 20, 2004, Germany, 14 pages.

ISA European Patent Office, International Search Report and Written Opinion Issued in Application No. PCT/US2015/054102, dated Jan. 18, 2016, WIPO, 14 pages.

Coetzer, Reinier Casper, "Development of a Robust Active Infrared-Based eye Tracking System", In In Doctoral Dissertation for Degree of Electrical, Electronic and Computer Engineering, Oct. 2011, 148 pages.

Zhu, et al., "Robust Real-Time Eye Detection and Tracking under Variable Lighting Conditions and Various Face Orientations", In Proceedings of Computer Vision and Image Understanding, vol. 98, Apr. 2005, 37 pages.

Gwon, et al., "Gaze Tracking System for User Wearing Glasses", In Proceedings of Sensors, vol. 14, No. 2, Jan. 27, 2014, pp. 2110-2134.

Rahayfeh, et al., "Eye Tracking and Head Movement Detection: A State-of-Art Survey", In IEEE Journal of Translational Engineering in Health and Medicine, vol. 1, Nov. 6, 2013, 12 pages.

Yang, et al., "A Gray Difference-based Pre-Processing for Gaze Tracking", In IEEE 10th International Conference on Signal Processing, Oct. 24, 2010, pp. 1293-1296.

IPEA European Patent Office, International Preliminary Report on Patentability Issued in PCT Application No. PCT/US2015/054102, Jan. 5, 2017, WIPO, 12 Pages.

Ebisawa, Y., "Unconstrained pupil detection technique using two light sources and the image difference method", Visualization and Intelligent Design in Engineering and Architecture II, Computations Mechanics Publications, Jun. 1995, 12 pages.

IPEA European Patent Office, Second Written Opinion Issued in Application No. PCT/US2015/054102, Sep. 1, 2016, WIPO, 10 pages.

* cited by examiner

GAZE TRACKING THROUGH EYEWEAR

BACKGROUND

Recent hardware and software advances have enabled new modes of natural user input (NUI) for computer systems. Gesture recognition, voice recognition, and gaze tracking are example NUI modes, which enable a user to interact intuitively with computer systems for various purposes and in various environments.

SUMMARY

Embodiments are disclosed that relate to distinguishing reflections from an eye and reflections from eyewear in an eye tracking system. One disclosed embodiment provides a method to furnish input representing gaze direction in a computer system operatively coupled to a vision system. In this embodiment, a first image of an eye at a first level of illumination is acquired by a camera of the vision system. The first image is obtained from the camera, and a second image of the eye corresponding to a second, different level of illumination is also obtained. Brightness of corresponding pixels of the first and second images is compared in order to distinguish a reflection of the illumination by the eye from a reflection of the illumination by eyewear. The input is then furnished based on the reflection of the illumination by the eye.

This Summary is provided to introduce a selection of concepts in simplified form that are further described below in the detailed description. This summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Gaze tracking is a form of NUI based on the direction of a user's gaze. In this approach, an image of the user's eye is acquired by a camera. Ocular features such as the pupil or limbus are located in the acquired image, and the gaze direction is computed based on the locations of such features. Gaze direction computed in this manner may be used to navigate a graphical user-interface, to launch a program, make a selection, move a character in a game, and so on. Although the desired ocular features may be identified in images of the naked eye, stray reflections from eyewear may be a source of interference. Such interference may reduce the accuracy of gaze-tracking input for users with eyewear. As used herein, the term 'eyewear' includes any type of appliance worn that places a see-through structure between the eye and at least a portion of a field of view of the eye. Examples include, but are not limited to, eyeglasses, sunglasses, visors, masks, goggles, contact lens systems and other on-eye devices, near-eye display systems that project virtual imagery in the wearer's field of view, etc.

Figure 1:
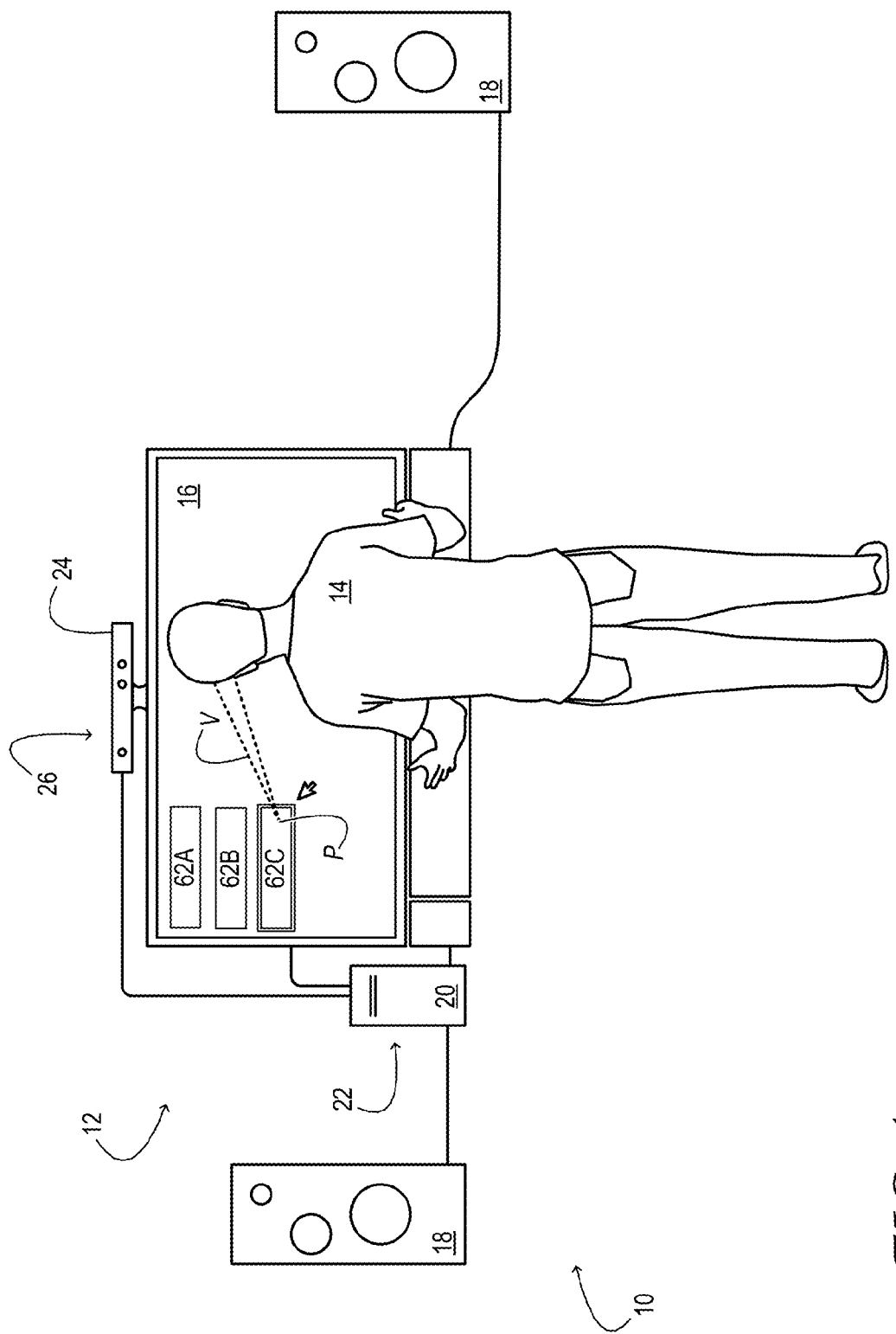
FIG. 1 shows aspects of an example environment in which a user's gaze is tracked and used as input in a computer system.

Examples are disclosed herein that may help to distinguish reflections of light from the naked eye and reflections of light from eyewear, and thus may facilitate eye tracking. FIG. 1 shows aspects of an example environment 10 in which a user's gaze is tracked and used as input in a computer system. The illustrated environment is a living room or family room of a personal residence. However, the systems and methods disclosed herein are equally applicable in other environments, such as workplace, retail and service environments. Environment 10 features a home-entertainment system 12 for the enjoyment of user 14. The home-entertainment system includes a large-format display 16 and loudspeakers 18, both operatively coupled to computer system 20. The nature of computer system 20 may differ in various implementations. In some examples, the computer system may be a video-game system or a multimedia system configured to play music and/or video. In other examples, the computer system may be a general-purpose computer system for internet access and productivity applications. Computer system 20 may be configured for any or all of the above purposes, and/or any other suitable purposes, without departing from the scope of this disclosure.

Computer system 20 may be configured to accept various forms of input from one or more users 14. As such, user-input devices such as a keyboard, mouse, touch-screen, gamepad, or joystick controller may be operatively coupled to computer system 20. Computer system 20 may also be configured to accept natural user input (NUI) from one or more users. To mediate the NUI, the illustrated computer system includes an NUI system 22. The NUI system is configured to capture various aspects of the NUI and provide corresponding actionable input to other constructs within the computer system. To this end, the NUI system receives low-level input from various sensory components of the computer system, which include vision system 24 and an optional listening system 26.

Listening system 26, if included, may comprise one or more microphones to pick up vocalization and other audible input from user 14. Vision system 24 may be configured to detect various forms of user input, such as gaze vectors V and focal point P, as well as hand and body gestures, facial features, etc. In the illustrated example, the vision system and listening system share a common enclosure; in other examples, they may be separate. In still other examples, the vision, listening and NUI systems may be integrated within computer system 20. The computer system and its peripheral components may be coupled via a wired communication link, as shown in the drawing, or in any other suitable manner.

Figure 2:
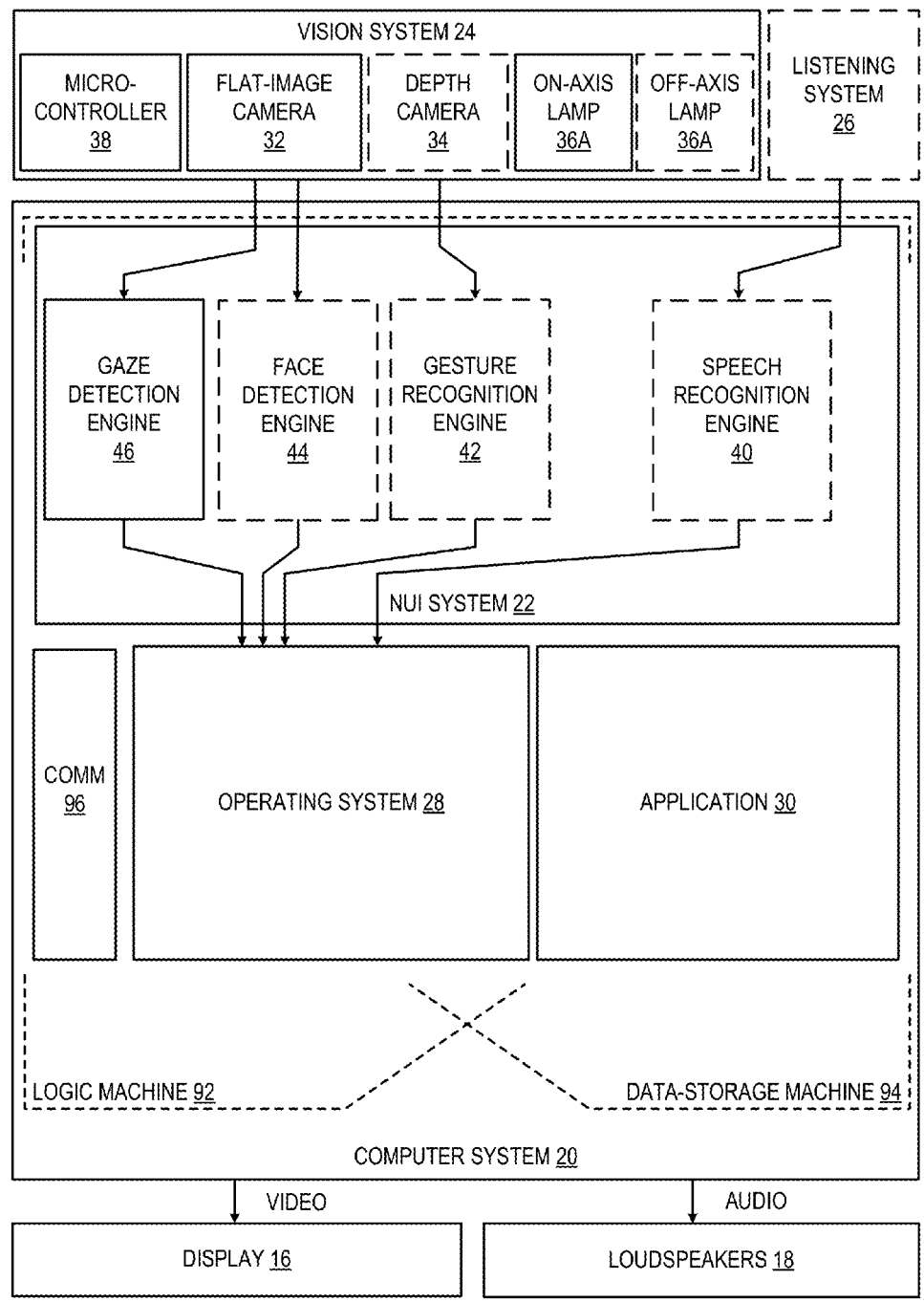
FIG. 2 shows aspects of an example computer system with an NUI system operatively coupled to a vision system.

FIG. 2 is a high-level schematic diagram showing aspects of an example of computer system 20, NUI system 22, vision system 24, and listening system 26. The illustrated computer system includes operating system (OS) 28, which may be instantiated in software and/or firmware. The computer system also includes one or more applications 30, such as a video game application, digital-media player, internet browser, photo editor, word processor, and/or spreadsheet application, for example. Computer system 20, NUI system 22, vision system 24, and listening system 26 may include suitable data storage, instruction storage, and logic hardware as needed to support their respective functions, as further described hereinafter.

In the example of FIG. 2, vision system 24 includes one or more flat-image cameras 32, and may also include one or more depth cameras 34. Each depth camera, if included, may be configured to acquire a time-resolved sequence of depth maps of user 14 and other aspects of environment 10. The vision system also includes on- and off-axis lamps 36A and 36B, which illuminate user 14 and the environment 10, to support imaging by the flat-image and/or depth cameras. Each lamp and camera of the vision system is operatively coupled to microcontroller 38. The microcontroller may be configured to control and triggers image acquisition by the cameras, and to control the illumination output of each lamp of the vision system.

Flat-image camera 32 detects light over a range of field angles and maps such angles onto a rectangular pixel array. In one example, the flat-image camera may detect light in a plurality of wavelength channels—e.g., red, green, blue, etc.—associated with a subset of the pixels of the array. Alternatively, a monochromatic flat-image camera may be used, to image visible, near-infrared (NIR), infrared (IR), and/or ultraviolet (UV) light in grayscale. Color or brightness values for all of the pixels exposed in the flat-image camera constitute collectively a digital image. In some examples, pixels of a flat-image camera may be registered to those of a depth camera.

As noted above, NUI system 22 processes low-level input (i.e., signal) from vision system 24 and optional listening system 26 to provide actionable, high-level input in computer system 20. For example, the NUI system may perform sound- or voice-recognition on audio signal from listening system 26. The voice recognition may generate corresponding text-based or other high-level commands to be received in OS 28 of the computer system. In the example shown in FIG. 2, the task of formulating a particular form of NUI from sensory data is assigned to particular NUI engines: speech-recognition engine 40, a gesture-recognition engine 42, face-recognition engine 44, and gaze-detection engine 46. Each of these engines may be configured to furnish its associated form of input to the OS and/or applications of the computer system.

Figure 3:
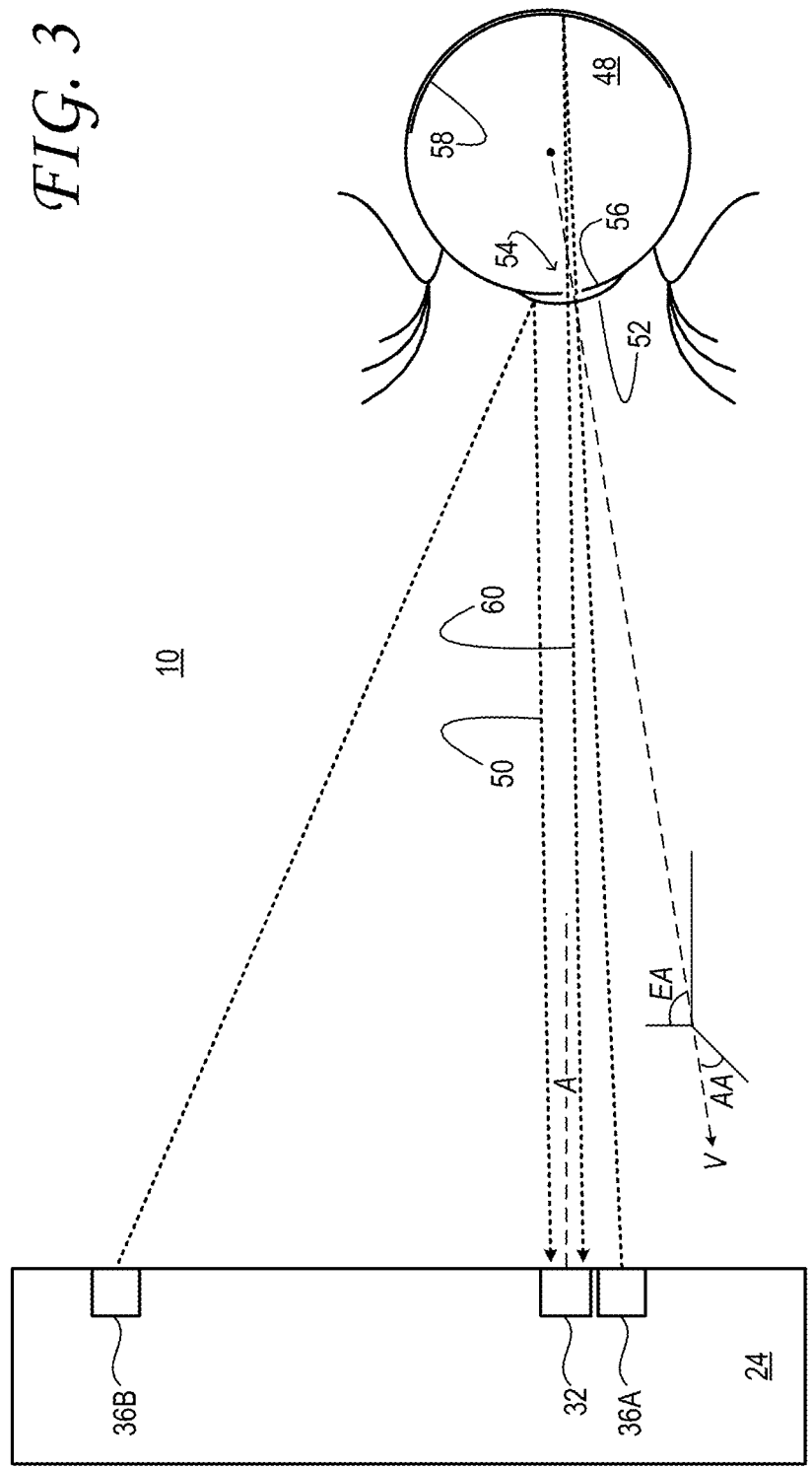
FIG. 3 shows aspects of an example vision system configured for gaze detection.

Turning now to FIG. 3, each lamp 36 of vision system 24 may comprise a light-emitting diode (LED), diode laser, discharge lamp, and/or other suitable light source. In environment 10, lamp 36A provides on-axis illumination of eye 48, and lamp 36B provides off-axis illumination. The terms 'on-axis' and 'off-axis' refer to the direction of illumination with respect to the optical axis A of flat-image camera 32.

On- and off-axis illumination may serve different purposes with respect to gaze tracking in environment 10. As shown in FIG. 3, off-axis illumination may create a specular glint 50 that reflects from cornea 52 of the user's eye. Off-axis illumination may also be used to illuminate the eye for a 'dark pupil' effect, where pupil 54 appears darker than the surrounding iris 56. By contrast, on-axis illumination from an IR or NIR source may be used to create a 'bright pupil' effect, where the pupil appears brighter than the surrounding iris. More specifically, IR or NIR illumination from on-axis lamp 36A may illuminate the retroreflective tissue of the retina 58 of the eye, which reflects the illumination back through the pupil, forming a bright image 60 of the pupil, as imaged by flat-image camera 32. In some examples, the flat-image camera may include a wavelength filter blocking transmission outside of the IR or NIR band of on-axis lamp 36A, to improve bright-pupil contrast in the presence of strong ambient light. Although FIG. 3 shows the on- and off-axis lamps schematically as point sources, it will be understood that these lamps may take any suitable form. For example, in some examples, on-axis lamp 36A may be configured in the form of an 'LED ring' surrounding the aperture of flat-image camera 32. In other words, the on-axis lamp may include a plurality of LEDs encircling the optical axis of the flat-image camera.

Gaze-detection engine 46 may be configured to process the image data from the flat-image camera to locate such features as the pupil center, pupil outline, and/or corneal glints. The locations of such features in the image data may be used as input parameters in a model—e.g., a polynomial model—that relates feature position to the gaze vector V of the eye. In examples where gaze is detected concurrently for both the right and left eyes, the point of intersection of the right and left gaze vectors may define the user's focal point P in three dimensions.

Returning briefly to FIG. 1, the drawing illustrates a scenario in which user 14 is navigating a UI presented on display 16 based on gaze direction. In this scenario, gaze-detection engine 46 has computed display screen coordinates (X, Y) corresponding to the point P that the user is gazing at. By shifting his gaze to other points on the display screen, the user can navigate among the various UI elements 62 of an application or OS executing on computer system 20.

Figure 4A:
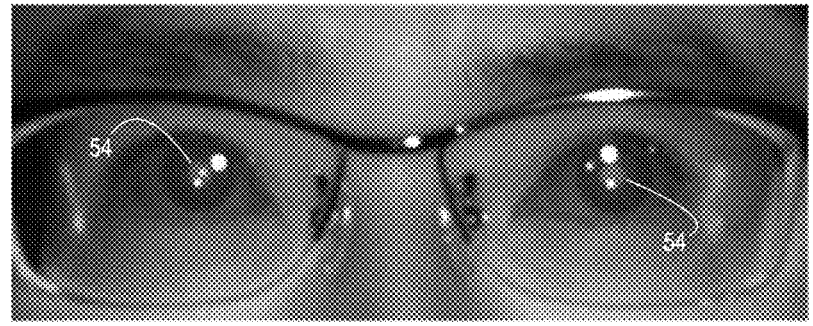
FIG. 4A shows an example image of a user's eyes obtained at a HIGH level of illumination.

The gaze-detection approach introduced above may be further refined to improve accuracy in cases where user 14 may be wearing eyewear, such as sunglasses, corrective lenses, bifocals, sunglasses, visors, contact lenses, near-eye display systems, and/or other eyewear. Positioned close to the eye, such eyewear may reflect the illumination from lamps 36A and 36B of vision system 24. Such reflection creates noise in the image data acquired by the vision system. The increased noise may make it more difficult for gaze-detection engine 46 to unambiguously locate the pupil and/or corneal glints, which may increase the error in the determined gaze direction. More specifically, reflection from eyewear may appear similar to the bright-pupil images created with on-axis illumination, so that the gaze-detection engine mistakes them for bright pupils. This effect is shown in FIG. 4A, where bright pupils 54 appear together with numerous reflections by the eyewear. A similar effect may occur when higher-angle illumination from off-axis lamp 36B is reflected by the eyeglasses and mistaken for a corneal glint. In general, when the reflection from the user's eyeglasses are relatively small in diameter and bright, they may appear similar to a corneal glint to a gaze-detection engine.

One approach to disambiguate the desired ocular reflections from eyeglass reflections is to remove the latter by post-processing of the acquired images. Plausible discrimination criteria include intensity, size, or geometry (shape) of the candidate reflection. However, any post-processing approach may be sensitive to image-quality and other noise issues, and may require excessive compute time. Moreover, noise removal based on geometric discrimination of noise reflections may fail to generalize among the expected range of use scenarios—e.g., different styles of eyeglasses worn by the user, which may include different lens curvatures, frame shapes, etc.

Thus, the disclosed examples may disambiguate the desired ocular reflections from eyeglass reflections by utilizing a series of images of the user's eye obtained at different illumination levels (i.e., intensities, powers). To this end, one, some, or all lamps 36 of vision system 24 may be configured to transition from providing a first level of illumination to providing a second, different level of illumination over a relatively short time interval, as further described below.

In one example, microcontroller 38 of vision system 24 may be configured to strobe on-axis lamp 36A and/or off-axis lamp 36B via pulse-width modulation (PWM). Two or more image frames are acquired at different brightness levels by assigning different PWM values to each frame. In other examples, the microcontroller may vary the voltage or current provided to the lamps, change the number of lamp elements (e.g., LEDs) receiving power, or modulate an electrooptical attenuator to change the level of illumination. Eye images at multiple brightness levels (HIGH+LOW, HIGH+INTERMEDIATE+LOW, etc.) are captured over a very short interval—e.g., 60 milliseconds (ms) or less, or 30 ms or less in some examples. The interval may be chosen, for example, to limit an extent of motion blur caused by possible movement of the eye between acquisition of the first and final images. During this interval, reflections from the ocular features of interest, such as pupils and glints, may decrease proportionally in intensity due to the decreasing illumination. However, the specular or near-specular reflections from the user's eyeglasses may saturate the receiving pixels of flat-image camera 32, even at the LOW or INTERMEDIATE brightness levels. Accordingly, a proportional decrease in brightness may not be observed for eyeglass reflections on transitioning from HIGH to INTERMEDIATE or LOW brightness. The pixels that do not darken proportionately may be removed from consideration in any suitable manner, to limit their impact on the subsequent gaze-tracking computation.

Figure 4B:
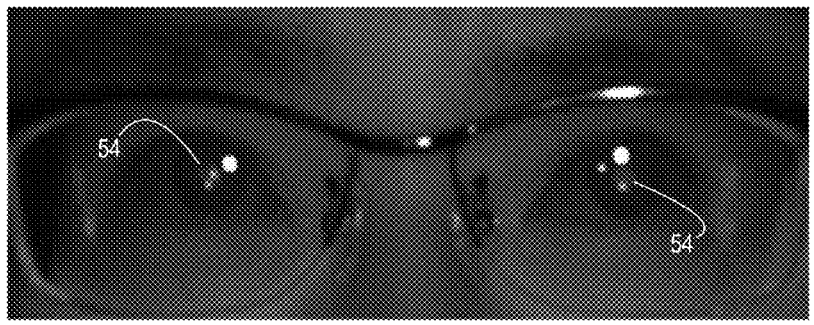
FIG. 4B shows an example image of a user's eyes obtained at a LOW level of illumination.

A side-by-side comparison of FIGS. 4A and 4B further illustrates the above approach. FIG. 4A shows an image acquired at HIGH brightness, and FIG. 4B shows an image acquired at LOW brightness. It can be seen that the reflection from the user's bright pupils 54 is weaker in FIG. 4B than in FIG. 4A, but the reflection from the user's eyeglasses is just as intense.

Gaze-detection engine 46 may be configured to manage a buffer of two or more images at different brightness levels, captured over a suitably short interval, such as 60 ms or less in some examples. The gaze-detection engine checks the brightness of the first (brighter) and second (darker) image, measuring every pixel. If a pixel has similar saturated brightness—e.g., differs by less than a threshold amount—or remains saturated in both images—the pixel then may, in some examples, be replaced with an average value of the brightness over the whole image (of FIGS. 4A and 4B, respectively) while all the remaining pixels (those not affected by eyeglass reflections) may keep their original values. In other examples, the pixels may not be replaced, but may be tracked or compensated for in another manner.

Figure 4C:
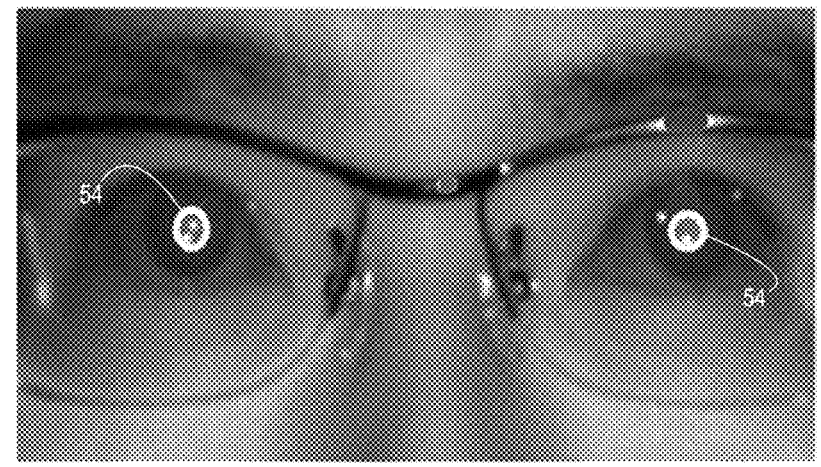
FIG. 4C shows an example result of excluding, from the image of FIG. 4A, reflections from the user's eyewear.

It will be noted that, as the image in FIG. 4A is brighter, the pupils have better contrast against the iris and are more easily detectable. In contrast, as FIG. 4B is darker, glints have better contrast against the pupils and are more easily detectable. The resulting processed images of FIG. 4A and FIG. 4B, after compensating for reflections of eyeglasses, are used as input for pupil detection and glint detection respectively. FIG. 4C shows a result of this procedure for applied to the HIGH and LOW intensity images of FIGS. 4A and 4B, where the white circles indicate the detected outlines of pupils 54.

Figure 5:
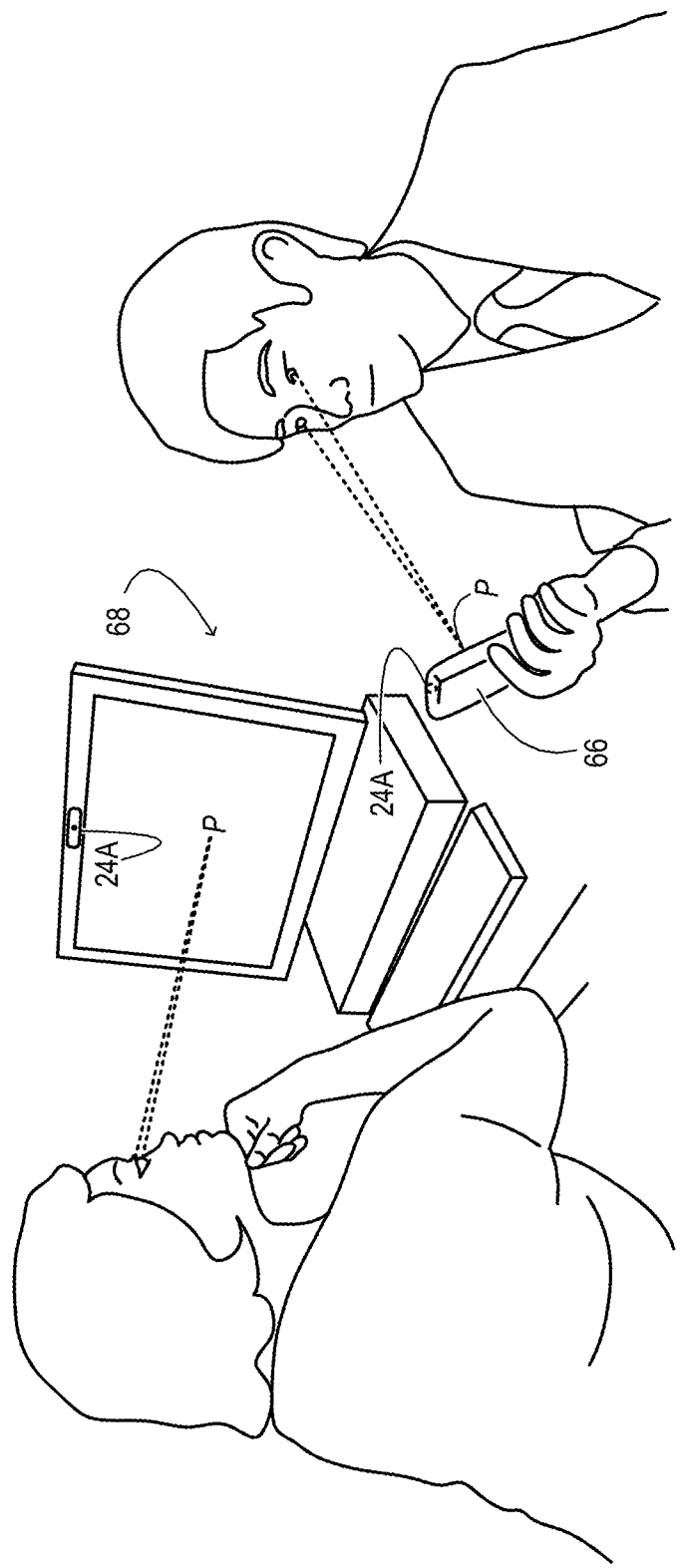
FIG. 5 shows aspects of additional example environments where a user's gaze is tracked and used as input in a computer system.

The foregoing drawings and description should not be interpreted in a limiting sense, for numerous other examples and use scenarios are contemplated as well. In particular, numerous other environments and form factors, besides that of FIG. 1, lay within the spirit and scope of this disclosure. For example, as shown in FIG. 5, analogous gaze tracking may be enacted in a smart phone 66 or desktop computer 68 with an appropriate vision system 24A mounted beneath the display bezel. In other examples, analogous gaze tracking may be enacted in a tablet or laptop computer with an integrated vision system.

Figure 6:
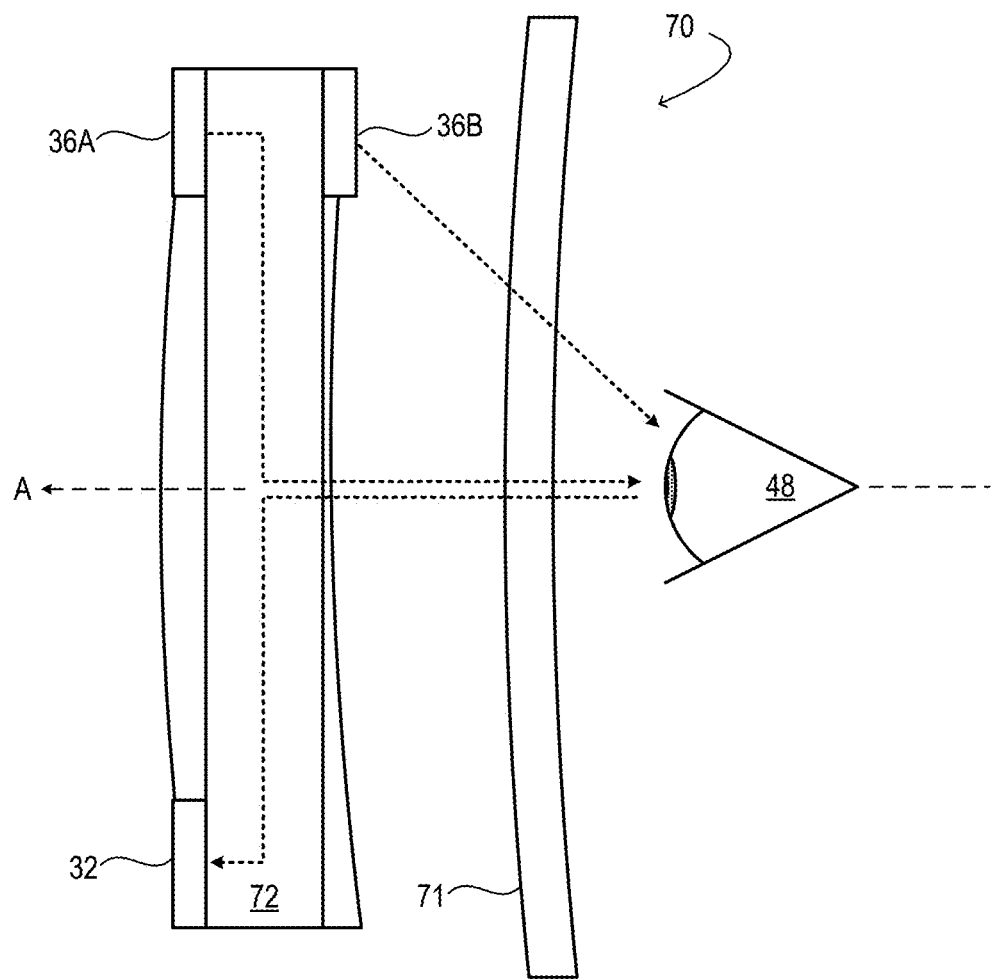
FIG. 6 shows aspects of another example vision system configured for gaze detection.

In still other examples, the vision system may be integrated in active headwear or eyewear worn by the user (who also may be wearing conventional eyeglasses). Such headwear or eyewear may further support a stereoscopic, near-eye display system. FIG. 6 shows an optical system 70 of a near-eye display system with integrated gaze tracking. In this example, the user is wearing additional corrective lenses 71. Flat-image camera 32 images light from on-axis IR or NIR lamp 36A reflected off the wearer's eye. An off-axis lamp 36B provides relatively high-angle illumination of the eye, to create a specular glint on the cornea of the eye, stimulate a dark-pupil effect, etc. Beam-turning optics integrated in optical system 70 enable the camera and the on-axis lamp to share a common optical axis A, despite their arrangement on the periphery of the optical system.

The approaches described herein may be extended to include other types of specular reflection than reflection from eyewear. In general, virtually any surface disposed between the user and the vision system may cause a bright, specular reflection that is distinguishable in the manner described herein. For example, specular reflection of vision-system illumination from a protective window (glass, acrylic, or polycarbonate sheet, hazmat shield, etc.) may be distinguished from an ocular reflection, for example, based on invariant detected brightness at two or more different illumination levels.

The configurations described above enable various methods for gaze detection to be enacted in a computer system operatively coupled to a vision system. Some such methods are now described with continued reference to the example configurations described above. It will be understood, however, that the methods here described, and others within the scope of this disclosure, also may be enabled by different configurations.

Figure 7:
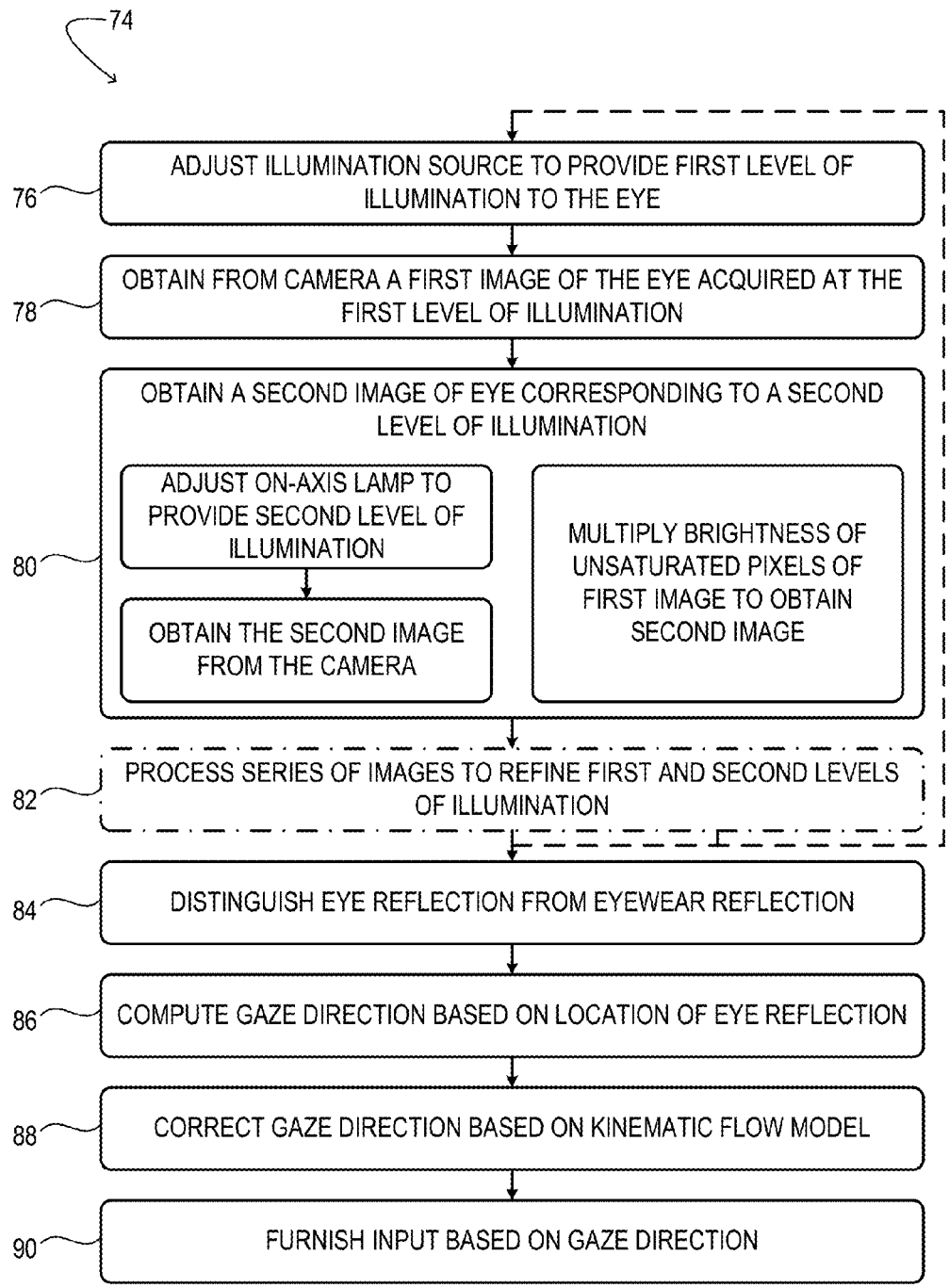
FIG. 7 illustrates an example method to furnish input responsive to gaze direction in a computer system.

FIG. 7 illustrates an example method 74 to furnish input responsive to gaze direction in a computer system operatively coupled to a vision system. At 76 of method 74, the output of an on-axis lamp of the vision system is adjusted to provide a first level of illumination to a user's eye prior to acquisition of a first image of the eye, for example, using one or more of the methods described above. The first level of illumination could be a relatively HIGH level of illumination, in one example.

At 78 a first image of the eye is obtained from a camera of a vision system. The first image is acquired by the camera during an interval in which the first level of illumination is provided to the eye. At 80 a second image of the eye corresponding to a second, different level of illumination is obtained. The second level of illumination may be lower or higher than the first level of illumination, and the second image may be obtained in different ways, in various examples.

In one example, the output of the on-axis lamp may be again adjusted to provide the second level of illumination for acquisition of the second image by the camera. The second image is then obtained from the camera. In another example, the second image of the eye is obtained by multiplying a brightness of each unsaturated pixel of the first image by a multiplication factor to obtain a corresponding pixel of the second image.

The multiplication factor may be greater than one to construct an overall brighter second image, or less than one to construct an overall darker second image. In one variant, multiplied brightness values of the second image may be clipped to the maximum brightness valid for the type of image encoding used by the camera. Further, pixels already saturated in the first image may be multiplied by a different factor (e.g., a factor of one), or otherwise masked. In this way, saturated pixels (that may correspond to specular reflection from the user's eyeglasses) are excluded from subsequent computations to determine the gaze direction.

The first and second images may be configured to reveal ocular reflections (e.g., bright pupils) at different, unsaturated brightness levels. This feature is used to distinguish the ocular features from eyeglass reflections (and, in some scenarios, from corneal glints due to off-axis illumination, which typically remain saturated, even at relatively low levels of illumination). However, it is not always possible to predict the appropriate first and second levels of illumination in advance of an unknown use scenario. For instance, different types of eyewear exhibit reflections of different reflectance. Further, the eyes of different individuals may require different levels of on-axis illumination to yield a bright-pupil response. Rather than apply the same two illumination levels for every user, gaze-detection engine 46 may be configured to analyze a series of three or more images acquired at different illumination levels, and then select appropriate first and second images to refine the first and second levels of illumination, as illustrated at 82 in FIG. 7. The images selected may be those, for example, which exhibit saturated eyeglass reflections, and strong but unsaturated (e.g., >30% saturated intensity, >50%, as examples) bright-pupil reflections. In this manner, the first and second levels of illumination, in method 74, may be selected based on ability to evoke and distinguish a bright pupil effect in the imaged eye, such levels differing for eyes of different users.

Another reason to provide a range of illumination levels across three or more acquired images may be to allow the system to respond to changing levels of ambient light in the wavelength band of the on-axis lamp. In this manner, the first and second levels of illumination may be selected based on ambient-light conditions. Providing a range of illumination levels also may help to distinguish the bright-pupil response from a corneal glint derived from off-axis illumination. Any suitable number of obtained images of the eye and corresponding illumination levels may be obtained, such as two, three, four, etc. This number may be dependent upon factors such as the frame rate utilized. In other words, faster image acquisition may enable a greater number of images to be acquired without experiencing the negative effect of motion blur due to eye movement.

Alternative modes of image/illumination-level selection may also be used at this stage of the method to address the challenges noted above. For example, once the appropriate illumination levels are revealed by analysis of the obtained images, this information may be fed back to earlier stages of the method to control which illumination levels are actually used when acquiring the first image, and obtaining the second image (whether by repeated image acquisition or by processing of the first image). This type of feedback may be used to reduce the number of redundant images obtained on each pass through the method, which may decrease the gaze-tracking latency. Even in cases where two images are obtained, feedback based on analysis of the obtained images may be used to refine the HIGH and LOW levels of illumination used for subsequent first and second images.

Continuing in FIG. 7, at 84 of method 74, a reflection of the illumination by the user's eye is distinguished from a reflection of the illumination by the user's eyewear. As noted above, the desired reflection of the illumination by the eye may constitute a bright-pupil response—i.e., a retroreflection from the retina of the user's eye, which passes back through the pupil and causes the pupil to appear bright relative to the surrounding iris. Alternatively, and equally important, the reflection by the eye may include a reflection by the iris itself, which causes the pupil to appear dark relative to the iris.

In one example embodiment, distinguishing eye from eyewear reflection may include comparing the brightness of corresponding pixels of the first and second images. In one example, corresponding pixels of the first and second images may be associated with the reflection of the illumination by the eye if the brightness of such pixels differs by more than a threshold amount (e.g., more than 5%, more than 10%, more than 10% of saturation, more than 10% of the maximum brightness, etc.). Conversely, the corresponding pixels may be associated with the reflection of the illumination by the eyewear if their brightness differs by less than a threshold amount (e.g., less than 5%, less than 1%, etc.). Such pixels may be masked from subsequent computation. In another example, corresponding pixels of the first and second images may be associated with reflection by the eyewear if both pixels are saturated. In yet another example, a machine-learned algorithm may be used to distinguish the reflection of the illumination by the eye from the reflection of the illumination by the eyewear.

At 86 gaze-direction input is computed based on a location, in the first or second image, of the reflection of the illumination by the eye, while excluding those pixels associated with the reflection of the illumination by the eyewear. In one example, the computed input includes an azimuth angle AA (in FIG. 3) and an elevation angle EA defining a direction of sight through the eye. Any suitable reference frame may be used for defining such angles. In one example, the reference frame has its origin at the entry pupil of flat-image camera 34 and one axis aligned with optical axis A. Naturally, the foregoing acts of method 74 may be enacted on both of the user's eyes, in a suitably configured vision system. When gaze vectors are available for both eyes, the coordinates of the user's focal point P may also be determined and included as input.

In some instances, on- or off-axis illumination of a user's eyewear will create a reflection that overlaps a desired ocular feature in the first or second image. When this occurs, exclusion of the pixels associated with the eyewear reflection could mask the ocular feature, or some portion thereof, potentially causing an interruption in gaze detection for the affected eye. It will be understood, however, that even a prolonged interruption in the availability of gaze input may be less disruptive to the user experience than delivering inaccurate gaze input. This may be especially true in examples where gaze is detected independently for each eye.

At optional step 88, the computed gaze direction is corrected based on a kinematic model to account for motion blur—viz., movement of the eye during the short time interval between obtaining the first and second images. The kinematic model may be an optical flow model, for example.

At 90, input including the detected gaze direction (and determined focal point, if available) is furnished to an appropriate consumer construct in the computer system—e.g., an OS or application of the computer system—based on the reflection of vision-system illumination by the eye. In view of the reflection discriminating effect of the disclosed method, the furnished input may be largely independent of reflection of the illumination by the user's eyewear. It will be understood that the examples described herein may be implemented in various different ways. For example, an image of a user's eye may be captured via at multiple exposures, such as by utilizing high dynamic range (HDR) imaging techniques, to achieve a greater dynamic range of luminosity in each image than with non-HDR techniques.

Further, some implementations may utilize an image sensing system configured to acquire two or more successive frames at some frame interval (e.g. every 30 ms) that helps to avoid impacting a desired frame rate. As a non-limiting example, an illumination system comprising one or more lasers may be used for illumination such that the illumination is provided at a first intensity for a time period (e.g., 2 ms) followed by a second, higher intensity for another time period (e.g., another 2 ms). During this illumination process, a first frame may be acquired in the first time period, and the second frame may be acquired during the second time period, such that both images of the eye are acquired before the image data is read. Any additional successive frames may be acquired in a similar manner. After the illumination process, the two or more image frames acquired may be read for the remaining duration of the frame interval. Any suitable hardware configuration may be used to acquire images in this manner. For example, a system may take the form of two juxtaposed cameras, which may or may not be internally constructed to share the same die.

As evident from the foregoing description, the methods and processes described herein may be tied to a computer system of one or more computing machines. Such methods and processes may be implemented as a computer-application program or service, an application-programming interface (API), a library, and/or other computer-program product. The reader is again referred to FIG. 2, which shows a non-limiting example of a computer system 20 used to support the methods and processes described herein. The computer system includes a logic machine 92 and an instruction-storage machine 94. The computer system also includes a display 16, communication system 96, and various components not shown the drawing.

Each logic machine 92 includes one or more physical logic devices configured to execute instructions. A logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Each logic machine 92 may include one or more processors configured to execute software instructions. Additionally or alternatively, a logic machine may include one or more hardware or firmware logic machines configured to execute hardware or firmware instructions. Processors of a logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices configured in a cloud-computing configuration.

Each data-storage machine 94 includes one or more physical, computer-memory devices configured to hold instructions executable by an associated logic machine 92 to implement the methods and processes described herein. When such methods and processes are implemented, the state of the data-storage machine may be transformed—e.g., to hold different data. A data-storage machine may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. A data-storage machine may include volatile, nonvolatile, dynamic, static, read/write, read-only, random-access, sequential-access, location-addressable, file-addressable, and/or content-addressable devices.

It will be appreciated that each data-storage machine 94 includes one or more physical devices. However, aspects of the instructions described herein alternatively may be propagated by a communication medium (e.g., an electromagnetic signal, an optical signal, etc.), as opposed to being stored via a storage medium.

Aspects of the logic machine(s) and data-storage machine(s) may be integrated together into one or more hardware-logic components. Such hardware-logic components may include field-programmable gate arrays (FPGAs), program- and application-specific integrated circuits (PA-SIC/ASICs), program- and application-specific standard products (PSSP/ASSPs), system-on-a-chip (SOC), and complex programmable logic devices (CPLDs), for example.

The term 'engine' may be used to describe an aspect of a computer system implemented to perform a particular function. In some cases, an engine may be instantiated via a logic machine executing instructions held by a data-storage machine. It will be understood that different engines may be instantiated from the same application, service, code block, object, library, routine, API, function, etc. Likewise, the same engine may be instantiated by different applications, services, code blocks, objects, routines, APIs, functions, etc. The term 'engine' may encompass individual or groups of executable files, data files, libraries, drivers, scripts, database records, etc.

Communication system 96 may be configured to communicatively couple the computer system to one or more other machines. The communication system may include wired and/or wireless communication devices compatible with one or more different communication protocols. As non-limiting examples, a communication system may be configured for communication via a wireless telephone network, or a wired or wireless local- or wide-area network. In some examples, a communication system may allow a computing machine to send and/or receive messages to and/or from other devices via a network such as the Internet.

It will be understood that the configurations and/or approaches described herein are exemplary in nature, and that these specific examples or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. Enacted in a computer system operatively coupled to a vision system, a method to furnish input representing gaze direction, the method comprising:
   from a camera of the vision system, obtaining a first image of an eye acquired under illumination of the eye by an emitter operated at a first power level;
   from the camera of the vision system, obtaining a second image of the eye acquired under the illumination of the eye by the emitter, the emitter being operated at a second, different power level;
   comparing brightness of corresponding pixels of the first and second images to distinguish a reflection of the illumination by the eye from a reflection of the illumination by eyewear, including selecting the first and second images from among three or more images of the eye acquired by the camera at mutually different power levels of the emitter so as to reveal an unsaturated, retroreflective bright-pupil response from the eye; and
   furnishing the input based on the reflection of the illumination by the eye.

2. The method of claim 1, wherein the reflection of the illumination by the eye includes a reflection from a retina of the eye, the reflection passing back through a pupil of the eye and causing the pupil to appear bright relative to a surrounding iris in the first image.

3. The method of claim 1, wherein the reflection by the eye includes a reflection by an iris of the eye, causing a pupil of the eye to appear dark relative to the iris in the first image.

4. The method of claim 1, further comprising computing the input based on a location, in the first image, of the reflection of the illumination by the eye, while excluding those pixels associated with the reflection of the illumination by the eyewear.

5. The method of claim 4, further comprising correcting the input based on a kinematic model to account for movement of the eye between obtaining the first and second images.

6. The method of claim 1, wherein the input furnished includes an azimuth angle and an elevation angle defining a direction of sight through the eye.

7. The method of claim 1, further comprising:
   associating the corresponding pixels of the first and second images with the reflection of the illumination by the eye if the brightness of such pixels differs by more than a threshold amount; and
   associating the corresponding pixels of the first and second images with the reflection of the illumination by the eyewear if the brightness of such pixels differs by less than a threshold amount.

8. The method of claim 1, further comprising associating the corresponding pixels of the first and second images with the reflection of the illumination by the eyewear if the corresponding pixels of the first and second images are both saturated.

9. The method of claim 1, wherein the first power level is selected based on ability to stimulate and distinguish a bright-pupil response from the eye.

10. The method of claim 1, wherein the first power level is selected based on ambient light conditions.

11. The method of claim 1, wherein the first and second images are selected from three or more images of the eye acquired by the camera at mutually different power levels of the emitter.

12. The method of claim 1, wherein comparing the brightness of the corresponding pixels includes using a machine-learned algorithm to distinguish the reflection of the illumination by the eye from the reflection of the illumination by the eyewear.

13. The method of claim 1, wherein the eye is a first of two eyes, and wherein the first and second images are images of the first eye, the method further comprising:
   from a camera of the vision system, obtaining a first image of a second eye acquired under illumination of the eye by an emitter operated at the first power level;
   from the camera of the vision system, obtaining a second image of the second eye acquired under the illumination of the eye by the emitter, the emitter being operated at the second power level;
   comparing brightness of corresponding pixels of the first and second images of the second eye to distinguish a reflection of the illumination by the second eye from a reflection of the illumination by eyewear; and
   furnishing the input based on the reflection of the illumination by the second eye and independent of the reflection of the illumination by the eyewear, such input including a determined focal point of the first and second eyes.

14. A system comprising:
   an illumination system including an emitter configured to illuminate an eye;
   a camera configured to acquire one or more images of the eye; and
   operatively coupled to the camera and the illumination system, a processor and associated computer memory, the computer memory holding instructions executable by the processor to
      from the camera of the vision system, obtain a first image of the eye under illumination of the eye by the emitter at a first power level;
      from the camera of the vision system, obtain a second image of the eye acquired under the illumination of the eye by the emitter, the emitter being operated at a second, different power level;
      compare brightness of corresponding pixels of the first and second images to distinguish a reflection of the illumination by the eye from a reflection of the illumination by eyewear, including selecting the first and second images from among three or more images of the eye acquired by the camera at mutually different power levels of the emitter so as to reveal an unsaturated, retroreflective bright-pupil response from the eye; and
      furnish input to a computer system based on the reflection of the illumination by the eye and independent of the reflection of the illumination by the eyewear.

15. The system of claim 14, further comprising instructions executable to capture one or more of the first image of the eye and the second image of the eye in multiple exposures.

16. The system of claim 14, wherein the instructions are executable to acquire the first image of the eye and the second image of the eye successively before reading the first image of the eye and the second image of the eye from the camera.

17. The system of claim 14, wherein the illumination system is configured to transition from providing the first power level of the emitter to providing the second power level of the emitter in thirty milliseconds or less.

18. Enacted in computer system operatively coupled to a vision system, a method to furnish input responsive to gaze direction of an eye, the method comprising:
- obtaining, from a camera of the vision system, a first image of the eye acquired under illumination of the eye by an emitter operated a first power level;
- obtaining from the camera a second image of the eye acquired under the illumination of the eye by the emitter, the emitter being operated at a second, different power level;
- comparing brightness of corresponding pixels of the first and second images to distinguish a reflection of the illumination by the eye from a reflection of the illumination by eyewear, including selecting the first and second images from among three or more images of the eye acquired by the camera at mutually different power levels of the emitter so as to reveal an unsaturated, retroreflective bright-pupil response from the eye; and
- furnishing the input based on the reflection of the illumination by the eye and independent of the reflection of the illumination by the eyewear.

19. The method of claim 18, wherein the emitter is a discrete light-emitting diode of the vision system, the method further comprising:
- adjusting the discrete light-emitting diode to provide the first power level prior to obtaining the first image; and
- adjusting the discrete light-emitting diode to provide the second power level prior to obtaining the second image.

* * * * *